(12) United States Patent
Strandberg et al.

(10) Patent No.: US 6,918,992 B1
(45) Date of Patent: Jul. 19, 2005

(54) FLUFF PULP FOR ABSORPTION PRODUCTS

(75) Inventors: Annica Strandberg, Gavle (SE); Stefan Hogman, Gavle (SE); Helena Tufvesson, Gavle (SE)

(73) Assignee: Korsnas AB, Gavle (SE)

( * ) Notice: Subject to any disclaimer, the term of this patent is extended or adjusted under 35 U.S.C. 154(b) by 0 days.

(21) Appl. No.: 09/926,340

(22) PCT Filed: Apr. 14, 2000

(86) PCT No.: PCT/SE00/00715

§ 371 (c)(1),
(2), (4) Date: Aug. 7, 2003

(87) PCT Pub. No.: WO00/66833

PCT Pub. Date: Nov. 9, 2000

(30) Foreign Application Priority Data

Apr. 16, 1999 (SE) ............................................... 9901361

(51) Int. Cl.$^7$ .............................................. D21H 17/68
(52) U.S. Cl. .................... 162/100; 162/181.8; 604/374; 604/375
(58) Field of Search .............................. 162/100, 181.8; 604/374, 375

(56) References Cited

U.S. PATENT DOCUMENTS 3,935,363 A    1/1976 Burkholder et al.
4,305,781 A   12/1981 Langley et al.
6,074,524 A  *  6/2000 Wu et al. .................... 162/100
6,667,424 B1 * 12/2003 Hamilton et al. ........... 604/375

FOREIGN PATENT DOCUMENTS

WO    WO 9817856 A1    4/1998

* cited by examiner

*Primary Examiner*—Peter Chin
(74) *Attorney, Agent, or Firm*—Bacon & Thomas

(57) ABSTRACT

A method of making a dry defibered fluff pulp suitable for absorption products is described. In the making of fluff pulp bentonite (montmorillonite), and optionally an additional inorganic particle compound, such as a synthetic silicate compound, is added to the pulp in an amount that in the final fluff pulp yields an amount of bentonite of 0.2 to 7 kg per ton fluff pulp and optionally an amount of the additional inorganic particle compound of 0.2 to 7 kg per ton fluff pulp, the total amount of retained particle additives amounting to no more than 8 kg per ton fluff pulp. Moreover, a thus made fluff pulp for absorption products, an absorption core for absorption products comprising such dry defibered fluff pulp and optionally a superabsorbent, and an absorption product comprising such a dry defibered fluff pulp and/or an absorption core are described. Moreover the use of such a dry defibered fluff pulp and/or absorption product for production of hygiene products, such as diapers, incontinent pads, sanitary napkins and wiper cloths are described.

9 Claims, 4 Drawing Sheets

FLUFF PULP FOR ABSORPTION PRODUCTS

The present invention relates to a method of making fluff pulp for absorption products, to such fluff pulp, absorption cores or absorption bodies, and absorption products such as diapers, incontinence pads, sanitary napkins and wiper cloths. Particularly, the invention relates to fluff pulp that includes added mineral matter of microparticle type, such as bentonite and the like, and to the use of such fluff pulp and such absorption products for the manufacture of diapers, sanitary napkins, incontinent pads and wiper cloths.

BACKGROUND

In hygiene products, such as diapers, sanitary napkins and incontinence pads, absorption bodies or absorption cores of so-called fluff are used. Fluff is made by dry defibering of cellulose pulp in form of long webs in rolls or sheets in bundles. To reduce the defibration energy and facilitate the defibering the pulp is provided before or on the wet machine with certain additives, which reduce the formation of bonds and lowers the friction between the fibers in the pulp. For example, for this purpose cationic tensides that have good adherence to the fibers are used, see e.g. U.S. Pat. No. 3,930,933. To reduce the negative effect of the tensides on the liquid absorption properties of the pulp and also on its brightness, the cationic tensides are often combined with e.g. nonionic tensides.

In resent years, an increased use of so-called synthetic superabsorbents has resulted in that the amount of cellulose fluff used in certain hygiene products has been radically reduced. These superabsorbents do not contribute to the integrity in the absorption pad and therefore it has become more and more important that the included cellulose fibers can contribute to the strength in the absorption cores of the hygiene products. Therefore, the so-called network strength of the cellulose fluff has become an even more preferred property. A good network strength is generally obtained if, in the process where the fluff pulp is dry defibered, an effective defibering or alternatively disintegration of fiber is achieved. Consequently, low so-called knot content is aimed at. Even though addition of softening organic tensides of cationic and nonionic type according to prior art yield a considerably improved defibering, they have a detrimental effect on the absorption properties of the fluff pulp.

In the patent SE 508 898 (Stora) is described a method of making a cellulose pulp by treatment with a non-polymeric aluminium salt. This treatment is said to improve the defibering properties of a fluff pulp.

For the purpose of obtaining in absorption products improved absorption in fluff pulp, the patent SE 500 858 (SCA) describes a method of producing fibers with increased specific surface by adhering hydrophilic chemicals consisting of positive inorganic ions in the form of different types of inorganic salts onto the fiber surface. There is i.a. mentioned aluminium as an example of positive inorganic ions, and as an example of an inorganic salt i.a. calcium carbonate is mentioned. The patent is directed to the positive effect that can be obtained on the absorption rate due to the increased specific surface. Thus, nothing is mentioned about the effects on defibering.

In WO 98/17856 is described a method of making a readily defibered cellulose pulp for use in absorbent products based on cellulose fluff. According to the description the method is based on that noncellulosic particles are added to the cellulose pulp together with a retention aid when the pulp is in an aqueous suspension. According to the claims so-called mineral fillers of e.g. clay, calcium carbonate or talc are used. A typical added amount is said to be 1–30% of the weight of the final cellulose product. In the application WO 98/17856 there are mentioned effects on defibration energy, knot content, absorption properties etc, but no effects on the network strength, which is an important property of the mechanical coherence of the absorbent products, have been presented.

The above mentioned methods with alum and calcium carbonate, respectively, according to SE 500 858 may have drawbacks due to limitations of the pH-intervals at which they are suitable. The complex equilibriums for the aluminium hydroxide systems lead to an optimum in the interval of pH 5.5–6.5. The method with calcium carbonate is used most advantageously at a pH above 7. Since both alum and carbonate, when they are in dry state in a final absorption product, can be affected by and partly dissolved by added liquid, unwanted effects of the dissolved chemicals may be obtained. It can be mentioned that the pH level in extracts, and possible interaction between the products and the skin, may be affected. From an end-user's point of view it may thus be an advantage if the desired effects can be obtained with a more inert additive than alum or calcium carbonate.

An addition of an inert component in the making of fluff pulp would also result in that the pH level in the pulp stock would not be critical. Any extra additives in the form of alkali or acid to adjust the pH would then not be needed.

DESCRIPTION OF THE INVENTION

It has now been revealed that an additive of inert character that gives the desirable effects is bentonite, an anionic microparticle product of montmorillonite with the basic composition $Al_2Si_4O_{10}(OH)_2 \cdot n\ H2O$. The addition of bentonite to the pulp stock in the making of fluff pulp is not pH dependent. Fluff pulp with added bentonite has proved to give a fluff pulp with low knot content at the defibering. Bentonite belongs to a group of additives that within the paper technology are primarily used in the retention agent system and are indicated as microparticles, with a typical particle size between 2.5 and 100 nm.

Thus, the present invention is i.a. directed to a method of making a dry defiberable fluff pulp which is suitable for absorption products, wherein, in the preparation of the fluff pulp, bentonite (montmorillonite) and optionally an additional inorganic particle compound, is added to the pulp in an amount that in the final fluff pulp yields an amount of bentonite of 0.2 to 7 kg per ton fluff pulp, the total amount of retained particle additive amounting to no more than 8 kg per ton fluff pulp.

In an embodiment of the invention the bentonite and the optional additional inorganic particle compound are added in such amounts that the retained amount of bentonite and the retained amount of particle compound, respectively, each lies in the range of 0.5 to 3.0 kg per ton fluff pulp. The particle compound used is e.g. a synthetic silicate compound, kaolin, talc or a carbonate.

At the making of the fluff pulp according to the invention, the bentonite and the optional particle compound are usually added to the wet pulp stock at a pH decided by the normal working optimum of the production process. The addition of bentonite (montmorillonite) to the wet pulp stock in the pulp making process is made suitably in the wet end on a wet machine (drying machine) before the outflow of the stock on the wet machine.

After dry defibering, the cellulose fluff produced according to the invention has unique properties that i.a. yields, in one of the analytic methods standardized for fluff pulp, a significantly lower knot content than an untreated pulp. Generally a reduced knot content in a defibered fluff is considered to be favorable for the network strength of the fluff. As is evident from the examples, which are described below, tests performed with higher additions of bentonite result in lower network strength than untreated reference pulp. Thus, the results indicate that an optimum with regard to the knot content and network strength is found in the interval of added bentonite that is indicated above and that is evident from the appended claims.

The underlying mechanisms of the observed optimum are not yet revealed, but a conceivable explanation could be that the microparticles of bentonite adhere on the surface of the cellulose fibers at the making of the fluff pulp in the wet process on the wet machine and thus increase the distance between adjacent cellulose fiber surfaces. Thus, the possibilities for hydrogen bonds between fibers are reduced, and the pulp shows a better defibering result at the dry defibering. If on the other hand the amount of bentonite particles on the fiber surface becomes too big the fibers may obtain a layer of smooth particles on the surface that reduces the friction between the fibers, which results in that the strength of the dry network is reduced.

Further, measured sheet properties show that the pulp with increased addition of bentonite gets lower burst strength and lower required defibration energy in the process where the pulp is dry defibered.

The treatment with bentonite has given these advantages without deteriorating the absorbent properties of the fluff, which, however, is the case with traditional softening additive chemicals.

The invention is also directed to a fluff pulp for absorption products that contains bentonite (montmorillonite), and optionally an additional inorganic particle compound, in an amount of bentonite of 0.2 to 7 kg per ton fluff pulp and optionally an amount of the additional inorganic particle compound of 0.2 to 7 kg per ton fluff pulp, the total amount of retained particle additive amounting to no more than 8 kg per ton dry defibered fluff pulp.

In an embodiment of the invention the fluff pulp comprises bentonite and the optional particle compound, respectively, in an amount of each in the range of 0.5 to 3.0 kg per ton dry defibered fluff pulp, and the particle compound is e.g. a synthetic silicate compound.

In addition, the invention is directed to an absorption core for absorption products, which comprises a dry defibered fluff pulp according to the invention and optionally a superabsorbent.

Moreover, the invention is directed to an absorption product, which comprises a dry defibered fluff pulp according to the invention and/or an absorption core according to the invention. Examples of absorption products or sanitary products are hygiene products, such as diapers, sanitary napkins, incontinence pads including bed pads and wiper cloths.

The invention is additionally directed to the use of a fluff pulp according to the invention, or an absorption body according to the invention, for the manufacture of absorption products, mainly hygiene products, such as diapers, incontinence pads, sanitary napkins and wiper cloths.

The invention will now be further illustrated by the following examples. These examples should not in any way be considered to limit the scope of the invention disclosed in the appended claims.

SHORT DESCRIPTION OF THE DRAWINGS

EXAMPLE 1

Figure 1:
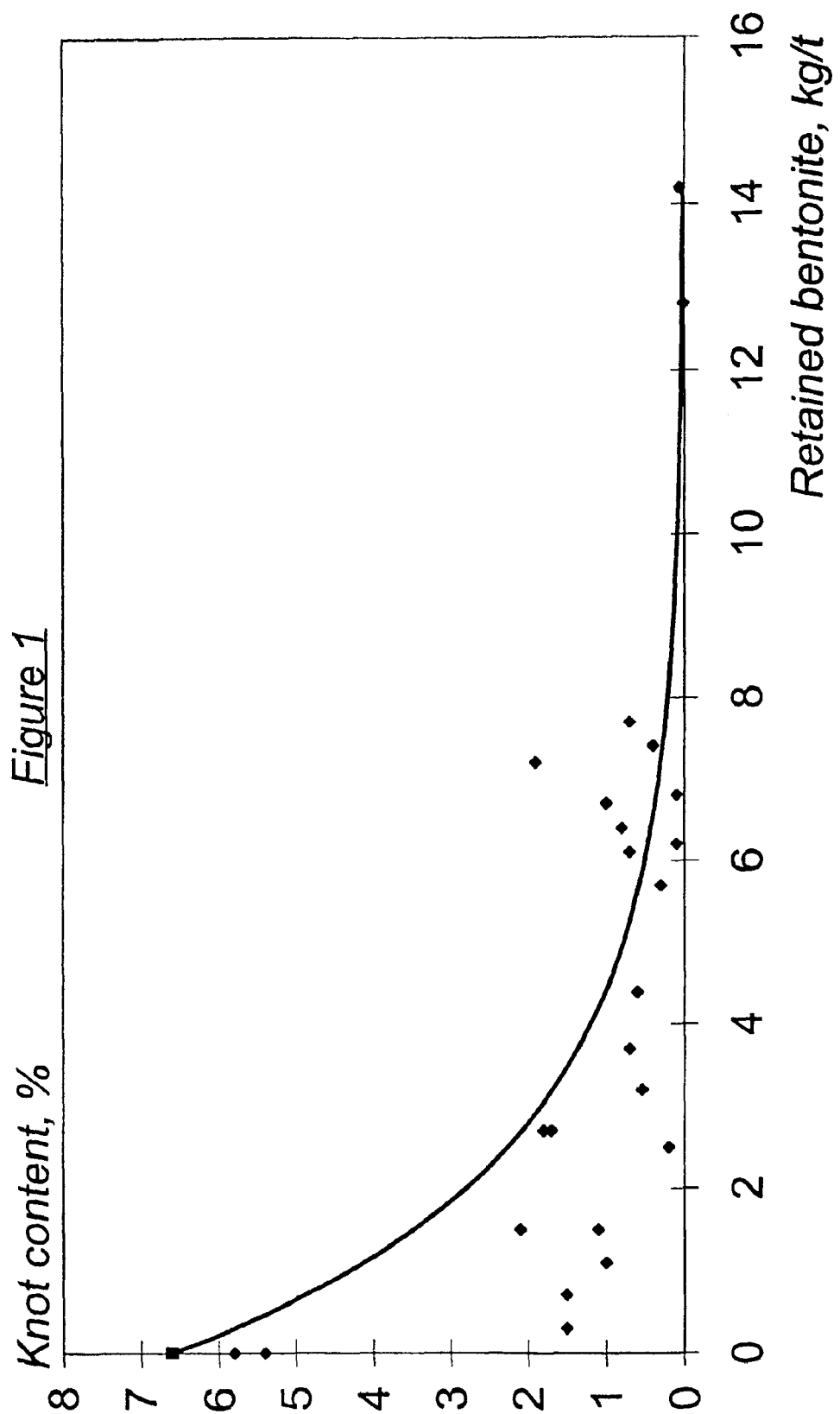
FIG. 1 shows a diagram where the knot content is plotted against retained amount of bentonite.

Bleached softwood pulp was used for making fluff pulp sheets with a grammage of approximately 750 $g/m^2$ in laboratory tests. In the tests with bentonite varying amounts of 3–30 kg/t of the product Hydrocol MD from Allied Colloids were added. According to the declaration from the supplier the product contains 94–98% sodium bentonite. In the laboratory tests cellulose fibers were added to tap water that had been pH adjusted to 6.5. Retention agent of the type BMB-1310 from Eka Chemicals and Hydrocol MD were added, whereupon the pH was checked and adjusted. The suspension was stirred for a total of 10 minutes. Fluff pulp sheets were made in sheet form with a pulp concentration of 0.1%. After compression and drying the sheets were defibered in a laboratory hammer mill of the Kamas H-01 type. The tests were evaluated by the use of SCAN methods as appropriate, otherwise with in-house standard methods.

For determination of the network strength property a method developed by Papirindustriens Forskningsinstitutt, PFI in Norway (1981) has been used. The method is commonly used in this field but has not been adopted as national or international standard. According to the method a cylindrical test piece is formed of the defibered fluff pulp with the diameter of 50 mm and weight of 1 g. The test piece is mounted in a sample holder in an apparatus for testing tensile and compression strength. The sample holder of the test apparatus has a mobile plate of steel with the diameter of 20 mm mounted on an axis. This plate puts a load on the center of the test piece when the test piece of fluff is tested. At testing, the plate is guided up through the mounted test piece at a velocity of 50 mm/min until the fiber network of the test piece is broken. The force with which the plate puts a load on the test piece during the testing is registered. The maximum force before the network brake is reported as "Network strength", unity N. Normally ten parallel tests are run.

The results from sheet and fluff testing of manufactured test pulps are given in Table 1.

It is evident from the results in table 1 that the positive effect of bentonite on the defibering result is strongly dependent on the amount of added or retained bentonite; i.e. defibration energy, burst strength and knot content are reduced with increasing amounts of bentonite. It is further evident that there seems to be an optimum with regard to the network strength of the fluff. The results indicate that this optimum is obtained at a retained amount of bentonite of between 1.1 and 2.5 kg/t. The results further show that the absorption properties at these bentonite amounts are at large unaltered compared to an untreated pulp. Also the specific surface of the fibers show moderate differences at these added amounts.

EXAMPLE 2

A mill trial was conducted on a pulp-drying machine, TM 6 at the Korsnäs plant in Gävle, Sweden. At the trial a 5 percent slurry of bentonite, Hydrocol MD was added to the pulp stock after the machine chest of the pulp preparation system. During the first part of the trial Hydrocol MD was dosed to the system in an amount corresponding to 5 kg bentonite per ton pulp, during the second part of the trial the dosage was 10 kg/t. Dried pulp sheets with a grammage of 750 g/m² were taken out for analysis according to the above disclosed methods. Reference samples from the process period before the trial were analyzed in the same way. The results from the analyses are given in Table 2.

The results from the mill trial, which are presented in table 2, confirm the results from the laboratory tests as to the defibering properties and primarily the knot content, even though the absolute levels of the knot contents are different from those in the laboratory tests. The difference in levels between laboratory tests and mill trials is a normal phenomenon and can be attributed to the difference in how ideally the sheets have been formed at the sheet forming stage. The results also show that the level of the network strength of the fluff has been retained due to the fact that the optimal added amount of bentonite has not been exceeded. Likewise the absorption properties of the fluff have been retained.

EXAMPLE 3

In laboratory tests bleached softwood pulp was used for making fluff pulp sheets with a grammage of approximately 800 g/m². At the tests 10 kg/t of the product Altonit SF (montmorillonite, sodium bentonite) from Kemira Kemi AB was added. In the laboratory tests cellulose fibers were added to the backwater from a drying machine for fluff pulp. The pH of the water was adjusted to 6.5. Three different types of cationic retention agents Fennopol with the different charges from Kemira Kemi AB were added at the test in the amount of 0.3 kg/t and for varying treatment periods. The suspension was stirred for a total of 10 minutes. Fluff pulp sheets were made into sheet form according to the same procedure as in example 1. After compression, drying and defibering in the same way as in example 1, analyses were performed and the results are summarized in Table 3.

The results in table 3 show that also the type of bentonite used in these tests gives clearly positive effects on the defibering, expressed as defibration energy or knot content. The retained amount of bentonite at a certain charge has here been greater than in earlier tests. Due to the high retention of bentonite, these tests show relatively low values for network strength, in analogy with the discussion in example 1.

EXAMPLE 4

Bleached softwood pulp was used for making fluff pulp sheets with a grammage of approximately 800 g/m² in laboratory tests. At the tests varying amounts of 3–30 kg/t of the product Hydrocol MD was added. In the laboratory tests cellulose fibers were added to the backwater from a drying machine for fluff pulp. The pH of the water was adjusted to 6.5. After the addition of the chemical the mixture was allowed to stand with stirring for 1 minute. A retention agent was not added in the tests. Fluff pulp sheets were manufactured in sheet form according to the same procedure as in example 1. After compressing, drying and defibering in the same way as in example 1, analyses were performed and the results are summarized in Table 4.

The results in table 4 confirm the earlier results, i.e. that with regard to the overall effect on knot content and network strength there is an optimal charge level of bentonite which corresponds to a retained amount of bentonite of 1.1–2.5 kg/t.

Figure 2:
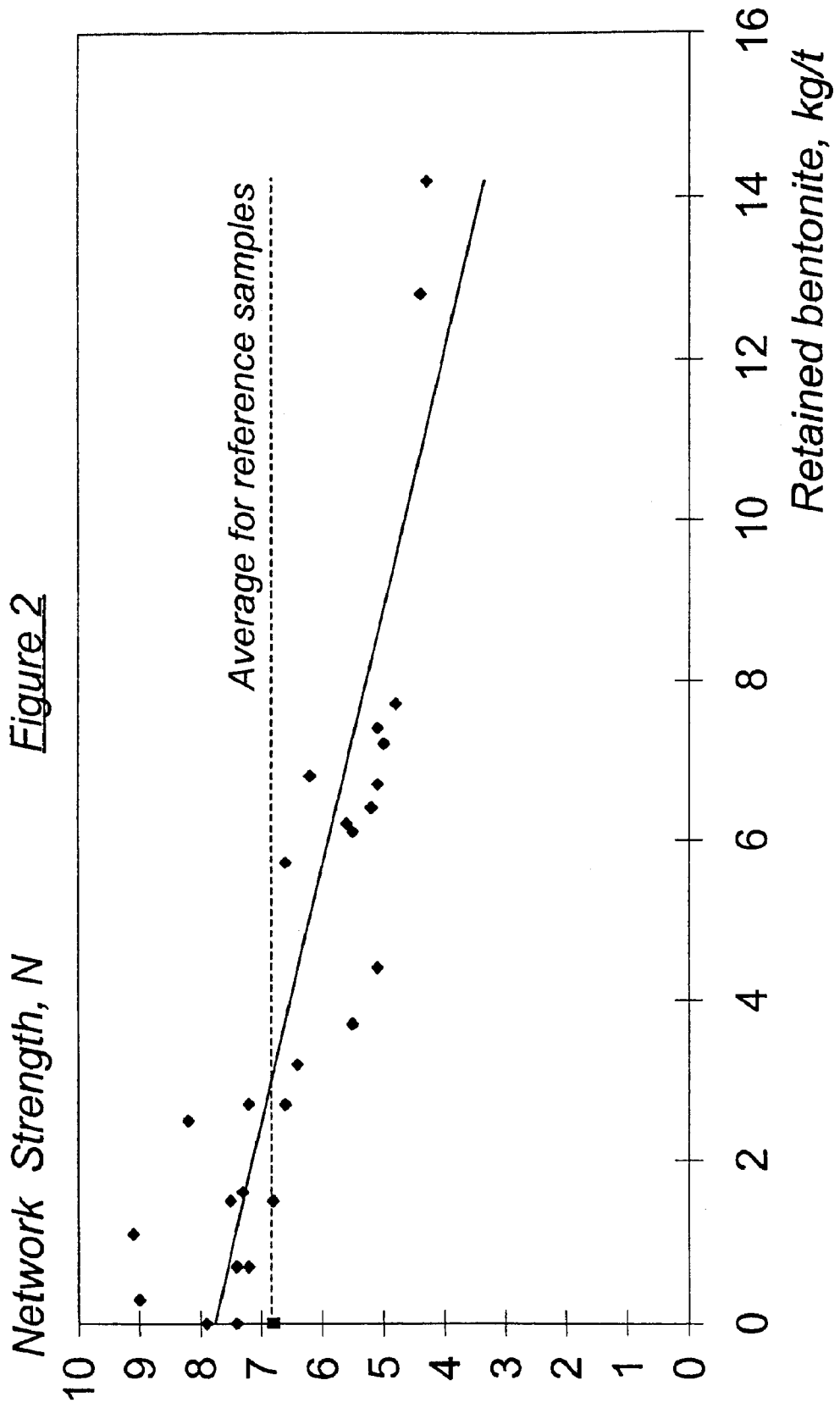
FIG. 2 shows a diagram where network strength is plotted against retained amount of bentonite.

The presented examples demonstrate that an optimal addition of bentonite in the making of fluff pulp gives an improvement of the defibering properties of the pulp, i.a. the knot content, without deteriorating the absorption properties of the pulp. The effects on knot content are evident from FIG. 1; from the results it is evident that there is needed only a relatively small amount of bentonite for obtaining a strong reduction of knot content. The reduced knot content contributes to improvement of the network strength of the defibered pulp, i.e. the fluff. From the examples is also evident that a too high addition of bentonite, over a level of approximately 3 kg/t as retained bentonite, deteriorates the network strength, see FIG. 2. The mechanisms for deterioration are not investigated. The overall effect of bentonite on knot content and network strength results in that there is an optimal interval of charge of bentonite.

EXAMPLE 5

Bleached softwood pulp was used for making fluff pulp sheets with a grammage of approximately 750 g/m² in laboratory tests. In the tests varying amounts of 7.5–10 kg/t of the products Altonit SF and Hydrocol MD, respectively, were added. In a couple of tests a combined addition of Hydrocol MD and a synthetic sodium magnesium aluminium silicate, "Hydrex A" from Zeofinn OY were also studied. Hydrex differs from Hydrocol i.a. by having a greater particle size. For the current variant a typical particle size of 4.5 µm is indicated. In the laboratory tests cellulose fibers were added to the backwater from a drying machine for fluff pulp. Retention agents according to Table 5 were added in certain tests. After addition of retention agent the mixture was left with stirring for 1 minute, whereupon the bentonite chemical was added. In the tests with the silicate Hydrex the order of charging was Retention agent—Hydrex—Hydrocol. Fluff pulp sheets were made in sheet form according to the same procedure as in example 1. After compressing, drying, and defibering in the same way as in example 1, analyses were performed and the results are summarized in Table 5.

As in the tests according to example 5, the tests in Table 5 give a relatively high amount of retained bentonite, which also results in low values for network strength. The tests in Table 5 show that also a combination of bentonite addition and addition of the silicate Hydrex has a positive influence on the network strength. A possible explanation to these effects may be that the larger silicate particles increase the friction between fibers, which is favorable for network strength.

EXAMPLE 6

Bleached softwood pulp was used for making fluff pulp sheets with a grammage of approximately 750 g/m² in laboratory tests. In the tests varying amounts of some different inorganic particle compounds were added. In addition to bentonite, Hydrocol MD, a kaolin clay, Kaovit from Thiele Scandinavia and a natural ground (GCC) calcium carbonate product, Hydrocarb 90 ME from Omya, were used. In the tests BMB-1310, a polyacryl amide from Eka Chemicals, or alternatively Alcofix 109, a Poly-DADMAC from Ciba Specialty Chemicals was added as retention agent. The charging of the particle compounds was up to 100 kg/t with a maximum retention of 75%. In the laboratory tests cellulose fibers were added to tap water before the chemical additives were mixed in. The retention agent was added and the mixture was allowed to stand with stirring for 1 minute (test number 6) alternatively 20 minutes (the remaining tests). Then the particle compound was added and the stirring was continued for 5 minutes, in example 6, however, only a short stirring was performed in conjunction with the addition of the particle compound. Fluff pulp sheets were made in sheet form according to the same procedure as in example 1. After compressing, drying and defibering in the same way as in example 1, analyses were performed and the results are summarized in Table 6.

Figure 3:
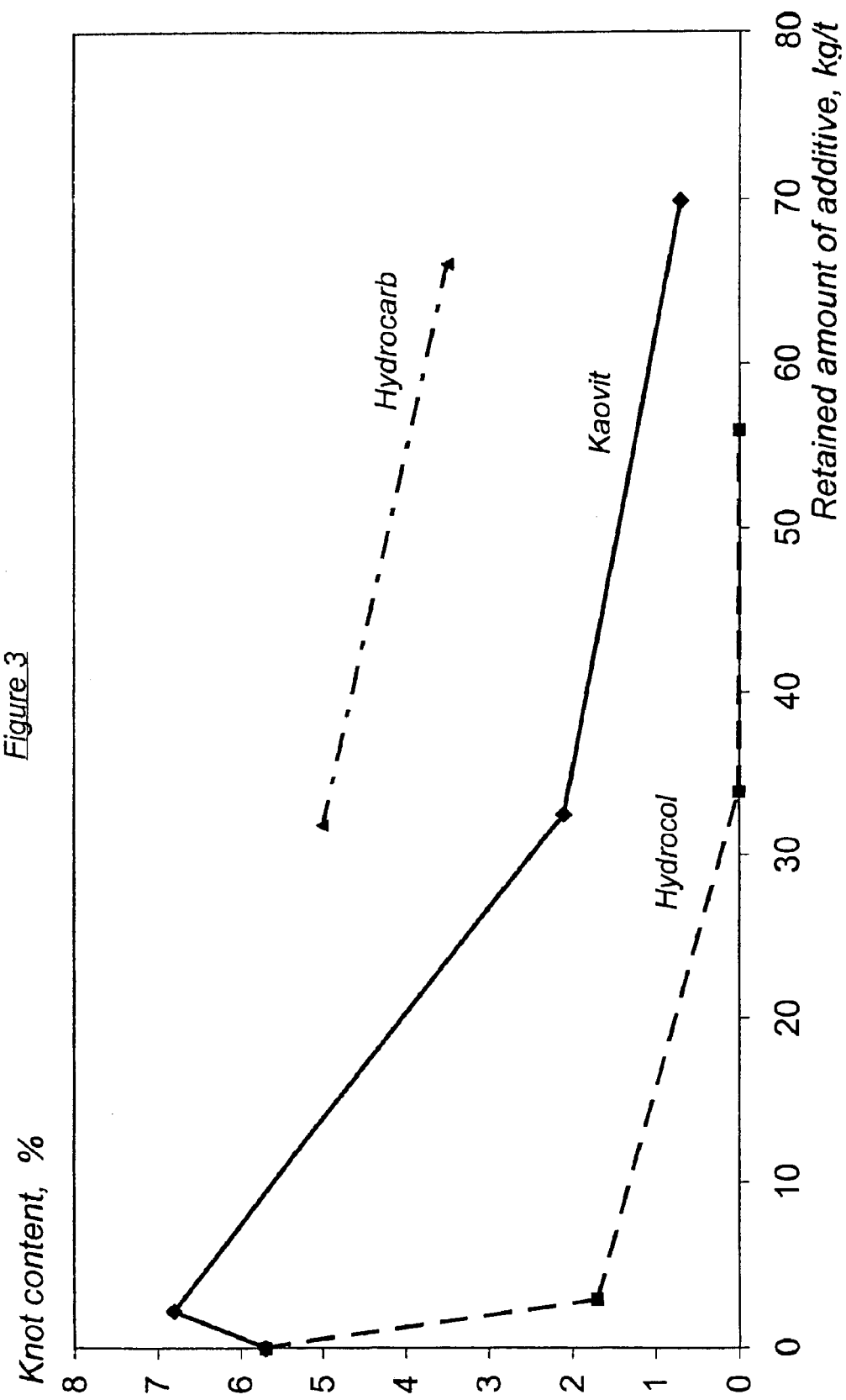
FIG. 3 shows a diagram where knot content is plotted against retained amount of Hydrocol, Kaovit and Hydrocarb, respectively.
Figure 4:
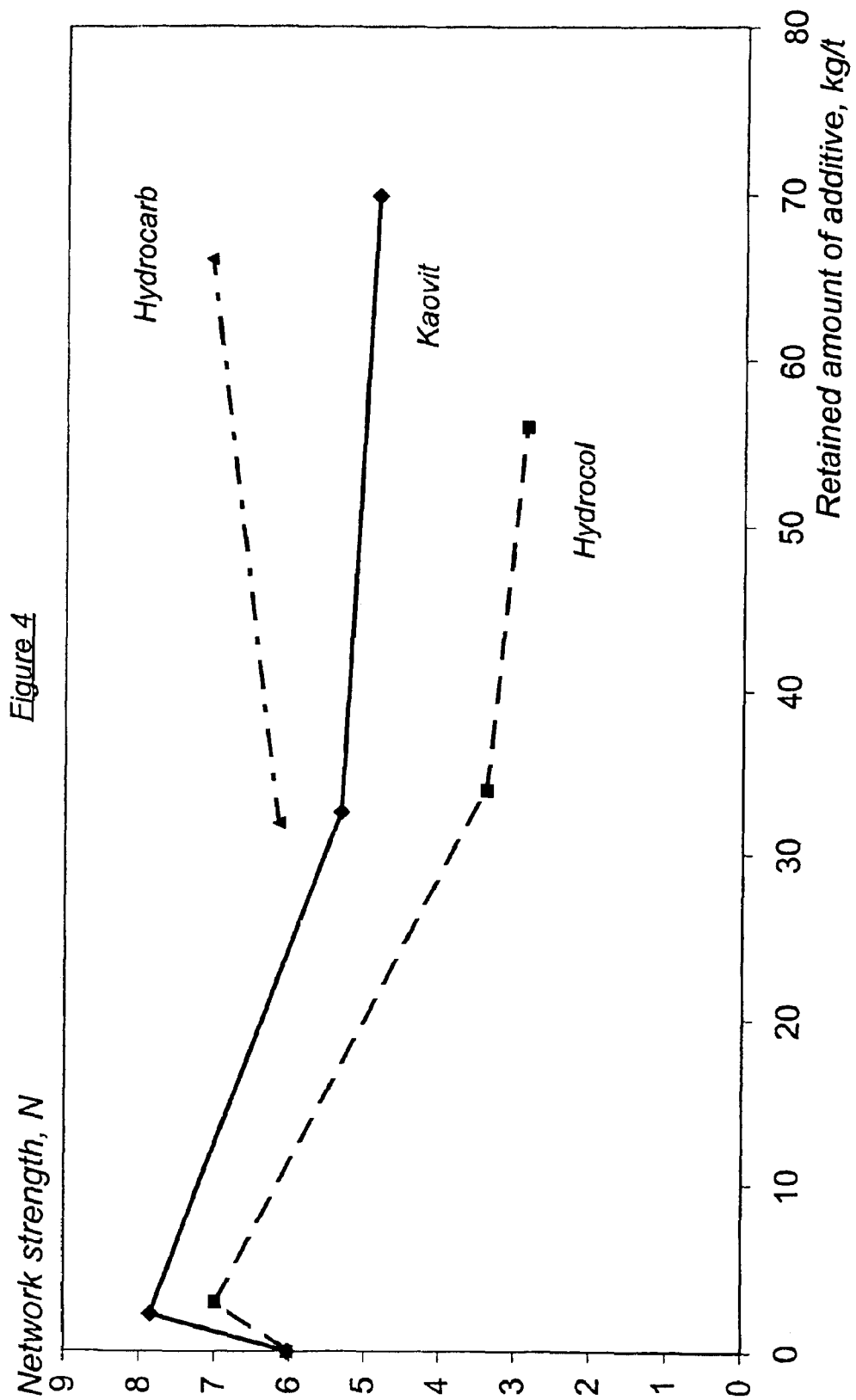
FIG. 4 shows a diagram where network strength is plotted against retained amount of Hydrocol, Kaovit and Hydrocarb, respectively.

According to the results in Table 6 the tests with bentonite gave a greater effect on defibering energy and knot content than the tests with kaolin. The carbonate tests show the smallest effect on knot content. Also in these tests the network strength shows higher values for the test which is performed with a low bentonite charge. Further, the test series with kaolin shows an optimum for network strength at a retained amount of additive of 2–3 kg/t. The results illustrated in the FIGS. 3 and 4 show that the different additions have different influence on the knot content, and in order to get the best combined effect of an additive on both knot content and network strength, the addition of the particle compound should not be too high. With regard to the network strength, the retained amount should be lower than approximately 7 kg/ton, or preferably 0.5–3.0 kg/ton, at addition of bentonite.

TABLE 2-continued

| Test No. | Reference | 1 | 2 |
|---|---|---|---|
| Bulk (SCAN-C 33), cm$^3$/g | 20.2 | 20.4 | 20.3 |
| Absorption time (SCAN-C 33), s | 1.6 | 1.7 | 1.7 |
| Absorption capacity (SCAN-C 33), g/g | 11.2 | 11.1 | 11.0 |
| Acquisition time, s | 16 | 19 | 19 |
| Liquid distribution 45° inclination | | | |
| Absorption 30 min, g/g | 5.1 | 5.4 | 5.5 |
| Distribution length, cm | 37 | 34 | 33 |
| Specific surface (BET), m$^2$/g | 0.64 | 0.64 | 0.73 |

TABLE 3

| Test No. | Reference | 1 | 2 | 3 | 4 |
|---|---|---|---|---|---|
| Dosage, kg/t | | | | | |
| Altonit SF Retention agent | — | 10 | 10 | 10 | 10 |
| Fennopol K 1488 R | — | 0.3 | — | — | — |
| Fennopol K 3400 R | — | — | 0.3 | 0.3 | — |
| Fennopol K 280 R | — | — | — | — | 0.3 |
| Treatment time with retention agent, min | — | 1 | 1 | 9 | 1 |
| Ash content (SCAN-C 6), % | 0.38 | 1.06 | 1.01 | 1.11 | 0.98 |
| Retained amount of bentonite, kg/t | — | 8.1 | 7.5 | 8.7 | 7.2 |
| Sheet properties | | | | | |
| Grammage (SCAN-P 6), g/m$^2$ | 792 | 820 | 806 | 814 | 810 |
| Density (SCAN-P 7), kg/m$^3$ | 553 | 547 | 533 | 544 | 536 |
| Defibration energy, | 172 | 141 | 137 | 155 | 155 |

TABLE 1

| Test No. | Reference | 1 | 2 | 3 | 4 | 5 | 6 | 7 |
|---|---|---|---|---|---|---|---|---|
| Dosage, kg/t | | | | | | | | |
| Hydrocol MD | — | 3 | 5 | 10 | 15 | 15 | 30 | 30 |
| BMB-1310 (retention agent) | — | — | — | — | — | 0.3 | — | 0.3 |
| pH | | 6.5 | 6.5 | 6.5 | 6.5 | 6.5 | 6.5 | 6.5 |
| Ash content (SCAN-C 6), % | 0.275 | 0.30 | 0.38 | 0.51 | 0.86 | 0.92 | 1.49 | 1.62 |
| Retained amount of bentonite, kg/t | — | 0.3 | 1.1 | 2.5 | 6.2 | 6.8 | 12.8 | 14.2 |
| Sheet properties | | | | | | | | |
| Grammage (SCAN-P 6), g/m$^2$ | 748 | 758 | 761 | 759 | 760 | 741 | 764 | 761 |
| Density (SCAN-P 7), kg/m$^3$ | 494 | 475 | 488 | 517 | 484 | 489 | 520 | 489 |
| Burst index (SCAN-P 24), kPa*m$^2$/g | 3.1 | 2.8 | 2.7 | 2.1 | 1.6 | 2.0 | 1.2 | 1.4 |
| Defibration energy, kJ/kg | 187 | 173 | 174 | 124 | 103 | 124 | 88 | 92 |
| Fluff properties | | | | | | | | |
| Knot content (SCAN-C 37), % | 7.5 | 1.5 | 1.0 | 0.2 | 0.1 | 0.1 | 0.01 | 0.06 |
| Network strength, N | 7.0 | 9.0 | 9.1 | 8.2 | 5.6 | 6.2 | 4.4 | 4.3 |
| Bulk (SCAN-C 33), cm$^3$/g | 19.3 | 19.5 | 19.3 | 18.1 | 16.8 | 17.5 | 15.1 | 15.2 |
| Absorption time (SCAN-C 33), s | 2.3 | 2.5 | 2.4 | 2.1 | 2.0 | 2.0 | 1.8 | 1.8 |
| Absorption capacity (SCAN-C 33), g/g | 10.8 | 10.3 | 10.1 | 9.3 | 9.1 | 9.3 | 8.1 | 9.2 |
| Specific surface (BET), m$^2$/g | 0.61 | | 0.70 | 0.53 | | | | |

TABLE 2

| Test No. | Reference | 1 | 2 |
|---|---|---|---|
| Dosage, kg/t | | | |
| Hydrocol MD | — | 5 | 10 |
| Sheet properties | | | |
| Grammage (SCAN-P 6), g/m$^2$ | 750 | 750 | 747 |
| Defibration energy, kJ/kg | 178 | 173 | 166 |
| Burst index (SCAN-P 24), kPa*m$^2$/g | 1.5 | 1.5 | 1.3 |
| Ash content (SCAN-C 6), % | 0.14 | 0.21 | 0.29 |
| Retained amount of bentonite, kg/t | — | 0.7 | 1.6 |
| Fluff properties | | | |
| Knot content (SCAN-C 37), % | 15 | 11 | 6 |
| Network strength, N | 7.5 | 7.4 | 7.3 |

TABLE 3-continued

| Test No. | Reference | 1 | 2 | 3 | 4 |
|---|---|---|---|---|---|
| kJ/kg | | | | | |
| Fluff properties | | | | | |
| Knot content (SCAN-C 37), % | 5.1 | 1.9 | 1.0 | 0.7 | 0.8 |
| Network strength, N | 6.1 | 5.0 | 5.1 | 4.8 | 5.2 |

TABLE 4

| Test No. | Reference | 1 | 2 | 3 | 4 | 5 |
|---|---|---|---|---|---|---|
| Dosage, kg/t | | | | | | |
| Hydrocol MD | — | 3 | 5 | 10 | 15 | 30 |
| pH | | 6.5 | 6.5 | 6.5 | 6.5 | 6.5 |
| Ash content (SCAN-C 6), % | 0.225 | 0.22 | 0.17 | 0.29 | 0.37 | 0.53 |
| Retained amount of bentonite, kg/t | — | 0 | 0 | 0.7 | 1.5 | 3.2 |
| Sheet properties | | | | | | |
| Grammage (SCAN-P 6), g/m$^2$ | 814 | 839 | 827 | 833 | 810 | 817 |
| Density (SCAN-P 7), kg/m$^3$ | 522 | 523 | 530 | 525 | 515 | 522 |
| Defibration energy, kJ/kg | 177 | 180 | 177 | 169 | 152 | 133 |
| Fluff properties | | | | | | |
| Knot content (SCAN-C 37), % | 6.5 | 5.8 | 5.4 | 1.5 | 1.1 | 0.5 |
| Network strength (dry), N | 6.3 | 7.9 | 7.4 | 7.2 | 7.5 | 6.4 |

TABLE 5

| Test No. | Reference | 1 | 2 | 3 | 4 | 5 | 6 | 7 | 8 | 9 | 10 |
|---|---|---|---|---|---|---|---|---|---|---|---|
| Dosage, kg/t | | | | | | | | | | | |
| Altonit SF | — | 7.5 | 10 | 7.5 | 10 | — | — | — | — | — | — |
| Fennopol K3400R (retention agent) | — | — | — | 0.3 | 0.3 | — | — | — | — | — | — |
| Hydrocol MD | — | — | — | — | — | 7.5 | 10 | 7.5 | 10 | 10 | 10 |
| Hydrocol 847 (retention agent) | — | — | — | — | — | — | — | 0.3 | 0.3 | 0.3 | 0.3 |
| Hydrex A | — | — | — | — | — | — | — | — | — | 5 | 10 |
| Ash content (SCAN-C 6), % | 0.28 | 0.51 | 0.76 | 0.79 | 0.90 | 0.42 | 0.54 | 0.63 | 0.70 | — | — |
| Retained amount of bentonite, kg/t | — | 2.7 | 5.7 | 6.1 | 7.4 | 1.5 | 2.7 | 3.7 | 4.4 | — | — |
| Sheet properties | | | | | | | | | | | |
| Grammage (SCAN-P 6), g/m$^2$ | 749 | 752 | 744 | 773 | 767 | 761 | 761 | 755 | 755 | 781 | 770 |
| Density (SCAN-P 7), kg/m$^3$ | 519 | 512 | 523 | 504 | 497 | 513 | 507 | 499 | 495 | 458 | 520 |
| Defibration energy, kJ/kg | 155 | 139 | 127 | 122 | 118 | 154 | 147 | 130 | 126 | 121 | 115 |
| Fluff properties | | | | | | | | | | | |
| Knot content (SCAN-C 37), % | 7.4 | 1.7 | 0.3 | 0.7 | 0.4 | 2.1 | 1.8 | 0.7 | 0.6 | 1.0 | 0.0 |
| Network strength, N | 7.2 | 7.2 | 6.6 | 5.5 | 5.1 | 6.8 | 6.6 | 5.5 | 5.1 | 7.8 | 7.4 |

TABLE 6

| Test No. | Reference | 1 | 2 | 3 | 4 | 5 | 6 | 7 | 8 | 9 |
|---|---|---|---|---|---|---|---|---|---|---|
| Dosage, kg/t | | | | | | | | | | |
| Kaovit | — | 4 | 50 | 100 | — | — | — | — | — | — |
| Hydrocarb 90 ME | — | — | — | — | 50 | 100 | — | — | — | — |
| Hydrocol MD | — | — | — | — | — | — | 4 | 50 | 100 | — |

TABLE 6-continued

| Test No. | Reference | 1 | 2 | 3 | 4 | 5 | 6 | 7 | 8 | 9 |
|---|---|---|---|---|---|---|---|---|---|---|
| BMB 1310 (Retention agent) | — | 0.3 | 3 | 3 | 3 | 3 | — | — | — | 3 |
| Alcofix 109 (Retention agent) | — | — | — | — | — | — | 0.3 | 3 | 3 | — |
| Retained amount of particle additive, kg/t | — | 2.3 | 32.5 | 69.9 | 31.8 | 66.0 | 3.0 | 33.9 | 56.0 | — |
| Sheet properties | | | | | | | | | | |
| Grammage (SCAN-P 6), g/m$^2$ | 727 | 738 | 758 | 792 | 752 | 782 | 732 | 762 | 778 | 738 |
| Density (SCAN-P 7), kg/m$^3$ | 485 | 505 | 484 | 516 | 504 | 515 | 479 | 551 | 607 | 511 |
| Defibration energy, kJ/kg | 185 | 185 | 189 | 137 | 198 | 184 | 136 | 76 | 67 | 231 |
| Fluff properties | | | | | | | | | | |
| Knot content (SCAN-C 37), % | 5.7 | 6.8 | 2.1 | 0.7 | 5.0 | 3.5 | 1.7 | 0 | 0 | 10 |
| Network strength, N | 6.0 | 7.9 | 5.3 | 4.9 | 6.2 | 7.1 | 7.0 | 3.4 | 2.9 | 6.4 |
| Bulk (SCAN-C 33), cm$^3$/g | 19.1 | 18.9 | 18.7 | 17.4 | 19.4 | 18.9 | 18.6 | 14.1 | 12.9 | 19.1 |
| Absorption time (SCAN-C 33), s | 2.4 | 2.6 | 2.2 | 2.0 | 2.4 | 2.3 | 2.5 | 1.8 | 1.7 | 2.6 |
| Absorption capacity (SCAN-C 33), g/g | 10.5 | 10.5 | 10.1 | 9.1 | 10.2 | 9.9 | 10.0 | 7.5 | 6.7 | 10.7 |

What is claimed is:

1. Method of making a dry defiberable fluff pulp which is suitable for absorption product, characterized in that in the preparation of the fluff pulp bentonite (montmorillonite), and optionally an additional inorganic particle compound, is added to the pulp in an amount that in the final fluff pulp give an amount of bentonite of 0.2 to 7 kg per ton fluff pulp and optionally an amount of the additional inorganic particle compound of 0.2 to 7 kg per ton fluff pulp, the total amount of retained particle additive amounting to no more than 8 kg per ton fluff pulp.

2. Method according to claim 1, characterized in that the amount of bentonite and the amount of particle compound, respectively, each lies in the range of 0.5 to 3.0 kg per ton fluff pulp.

3. Method according to claim 1, characterized in that the particle compound is a synthetic silicate compound.

4. Fluff pulp for absorbent products, comprising bentonite (montmorillonite), and optionally an additional inorganic particle compound, in an amount of bentonite of 0.2 to 7 kg per ton fluff pulp and optionally an amount of the additional inorganic particle compound of 0.2 to 7 kg per ton fluff pulp, the total amount of retained particle additive amounting to no more than 8 kg per ton dry defibered fluff pulp.

5. Fluff pulp for absorbent products, comprising bentonite (montmorillonite), and optionally an additional inorganic particle compound, in an amount of bentonite of 0.5 to 3.0 kg per ton dry defibered fluff pulp and optionally an amount of the additional inorganic particle compound of 0.5 to 3.0 kg per ton dry defibered fluff pulp, the total amount of retained particle additive amounting to no more than 8 kg per ton dry defibered fluff pulp.

6. Fluff pulp for absorbent products, comprising bentonite (montmorillonite), and optionally a synthetic silicate compound, in an amount of bentonite of 0.2 to 7 kg per ton fluff pull and optionally an amount of a synthetic silicate compound of 0.2 to 7 kg per ton fluff pulp, the total amount of retained particle additive amounting to no more than 8 kg per ton dry defibered fluff pulp.

7. Absorption core for absorption products, comprising a dry defibered fluff pulp according to claim 4 and optionally a superabsorbent.

8. An absorption product, comprising an absorption core of the defibered fluff pulp according to claim 4.

9. The absorption product according to claim 8, wherein the product is a diaper, incontinent pad, sanitary napkin or wiper cloth.

* * * * *